(12) United States Patent
Ashton et al.

(10) Patent No.: US 9,134,289 B2
(45) Date of Patent: Sep. 15, 2015

(54) APPARATUS FOR ON-LINE CONTINUOUS CHLORINE ANALYSIS IN TURBID WATER AND PROCESS STREAMS

(71) Applicant: Nalco Company, Naperville, IL (US)

(72) Inventors: Stephen Bernard Ashton, Chester (GB); Martin Seifert, Mayen (DE)

(73) Assignee: NALCO COMPANY, Naperville, IL (US)

( * ) Notice: Subject to any disclaimer, the term of this patent is extended or adjusted under 35 U.S.C. 154(b) by 373 days.

(21) Appl. No.: 13/826,144

(22) Filed: Mar. 14, 2013

(65) Prior Publication Data

US 2013/0192337 A1    Aug. 1, 2013

Related U.S. Application Data

(63) Continuation-in-part of application No. 12/951,179, filed on Nov. 22, 2010, now Pat. No. 9,016,110.

(51) Int. Cl.
  *G01N 33/18*    (2006.01)
(52) U.S. Cl.
  CPC .............. *G01N 33/18* (2013.01); *G01N 33/182* (2013.01)
(58) Field of Classification Search
  CPC .............................. G01N 33/18; G01N 33/182
  USPC ....................................................... 73/61.43
  See application file for complete search history.

(56) References Cited

U.S. PATENT DOCUMENTS

| | | | | |
|---|---|---|---|---|
| 5,362,650 A | * | 11/1994 | Harp | 436/125 |
| 6,245,224 B1 | * | 6/2001 | Enoki et al. | 210/87 |
| 6,444,172 B2 | * | 9/2002 | Fukunaga et al. | 422/68.1 |
| 2005/0276724 A1 | * | 12/2005 | Bremauer | 422/29 |
| 2007/0092406 A1 | * | 4/2007 | Ben David | 422/82.05 |
| 2008/0116144 A1 | * | 5/2008 | Vineyard et al. | 210/739 |

* cited by examiner

*Primary Examiner* — Peter MacChiarolo
*Assistant Examiner* — Nathaniel Kolb
(74) *Attorney, Agent, or Firm* — Benjamin Carlsen

(57) ABSTRACT

The invention is directed towards methods and apparatus for accurately detecting the presence and concentration of an oxidant in a turbid water sample. This method is very helpful in allowing accurate and efficient (not too much nor too little) amounts of microbe killing oxidants to be introduced to water supplies that require oxidants but which at present cannot be measured properly. The method comprises the steps of: passing the water through at least one filter array, passing the filtered water to an analyzer, and then returning from the analyzer a measurement of the concentration. The filter array comprises at least one filter constructed and arranged to remove turbidity inducing material but not oxidant from the water sample. The analyzer can be a commonly commercially available analyzer that currently cannot accurately measure the oxidant concentration if the water had not been so filtered. This method allows users to apply easily available oxidant measuring technology to applications such as paper mill water where it is needed but was previously was not applicable.

13 Claims, 2 Drawing Sheets

US 9,134,289 B2

APPARATUS FOR ON-LINE CONTINUOUS CHLORINE ANALYSIS IN TURBID WATER AND PROCESS STREAMS

CROSS-REFERENCE TO RELATED APPLICATIONS

This application is a continuation in part application of co-pending U.S. patent application Ser. No. 12/951,179 filed on Nov. 22, 2010.

STATEMENT REGARDING FEDERALLY SPONSORED RESEARCH OR DEVELOPMENT

Not Applicable.

BACKGROUND OF THE INVENTION

The present invention relates generally to methods of, and apparatus for accurately monitoring the amount of biocides and particular oxidants present in a given water volume. Oxidants such as sodium hypochlorite and other halogen-based compositions (including but not limited to Actibrom, BCDMH, and Stabrex) are frequently used to control the growth of microbial organisms and other biological deposit formations in water and industrial processes. Efficient and effective use of these compositions however requires that proper concentrations be maintained. This is best achieved by use of an online system that provides real time up to date concentration information.

One on-line method of monitoring the concentrations in water involves determining the amount of total halogen and free halogen residuals. This can be accomplished by a number of commercially available devices using various techniques. The HACH CL17 measures free and total chlorine using colorimetric method and N,N-diethyl-p-phenylenediamine (DPD) indicator reagent. Unfortunately, the use of such colorimetric and indicator reagents is limited to water systems with low solids and with turbidity values below 5 nephelometric turbidity units (NM). Paper process water typically has a solids content ranging from 0.1 to 0.5% even in the most clarified parts of the process, which greatly exceeds the limitations of available technology.

Another method is Oxidation-Reduction Potential (ORP). ORP however only gives an indirect measurement of oxidant concentration. Also because ORP is affected by factors other than just halogen concentration, under certain circumstances, and in particular in highly turbid environments it is inaccurate.

Yet another method is Amperometric measurements. Amperometric measurements use a conductive element sensor (typically having a copper and platinum or gold electrode). A small amount of potential is applied to the sensor electrodes. An electric charge is then generated by the chemical reduction of the oxidant. The resulting charge is in direct linear proportion to the amount of residual halogen present in the sample. Amperometric measurements however require membrane caps, which rapidly become fouled when continuously used in many industrial processes. As a result, Amperometric measurements are only of limited practical use.

It is therefore useful and desirable to provide methods and apparatus to better detect the concentration of oxidants in water samples. The art described in this section is not intended to constitute an admission that any patent, publication or other information referred to herein is "Prior Art" with respect to this invention, unless specifically designated as such, in addition, this section should not be construed to mean that a search has been made or that no other pertinent information as defined in 37 CFR §1.56(a) exists.

BRIEF SUMMARY OF THE INVENTION

To satisfy the long-felt but unsolved needs identified above, at least one embodiment of the invention is directed towards a method of accurately detecting the presence and concentration of an oxidant in a turbid water sample, the method comprising the steps of: 1) passing the water through a series of filter arrays, the filter array comprises at least one filter constructed and arranged to remove solids to an acceptable level (in line with requirements of the Chlorine analyser) and also reduce turbidity inducing material but not oxidant from the water sample with a cross-directional filter sheet, 2) then passing the filter array filtered water to a sample tank, the sample tank sized to allow continuous passage of water to an oxidant analyzer even when water is not passing thorough the filters, 3) passing the water to an oxidant monitor that would not be able to accurately measure the oxidant concentration if the water had not been filtered, and 4) returning from the monitor a measurement of the concentration. Optionally the sample can then be passed to a sample tank.

Additional features and advantages are described herein, and will be apparent from, the following Detailed Description.

BRIEF DESCRIPTION OF THE DRAWINGS

A detailed description of the invention is hereafter described with specific reference being made to the drawings in which.

For the purposes of this disclosure, like reference numerals in the figures shall refer to like features unless otherwise indicated. The drawings are only an exemplification of the principles of the invention and are not intended to limit the invention to the particular embodiments illustrated.

DETAILED DESCRIPTION OF THE INVENTION

Figure 1:
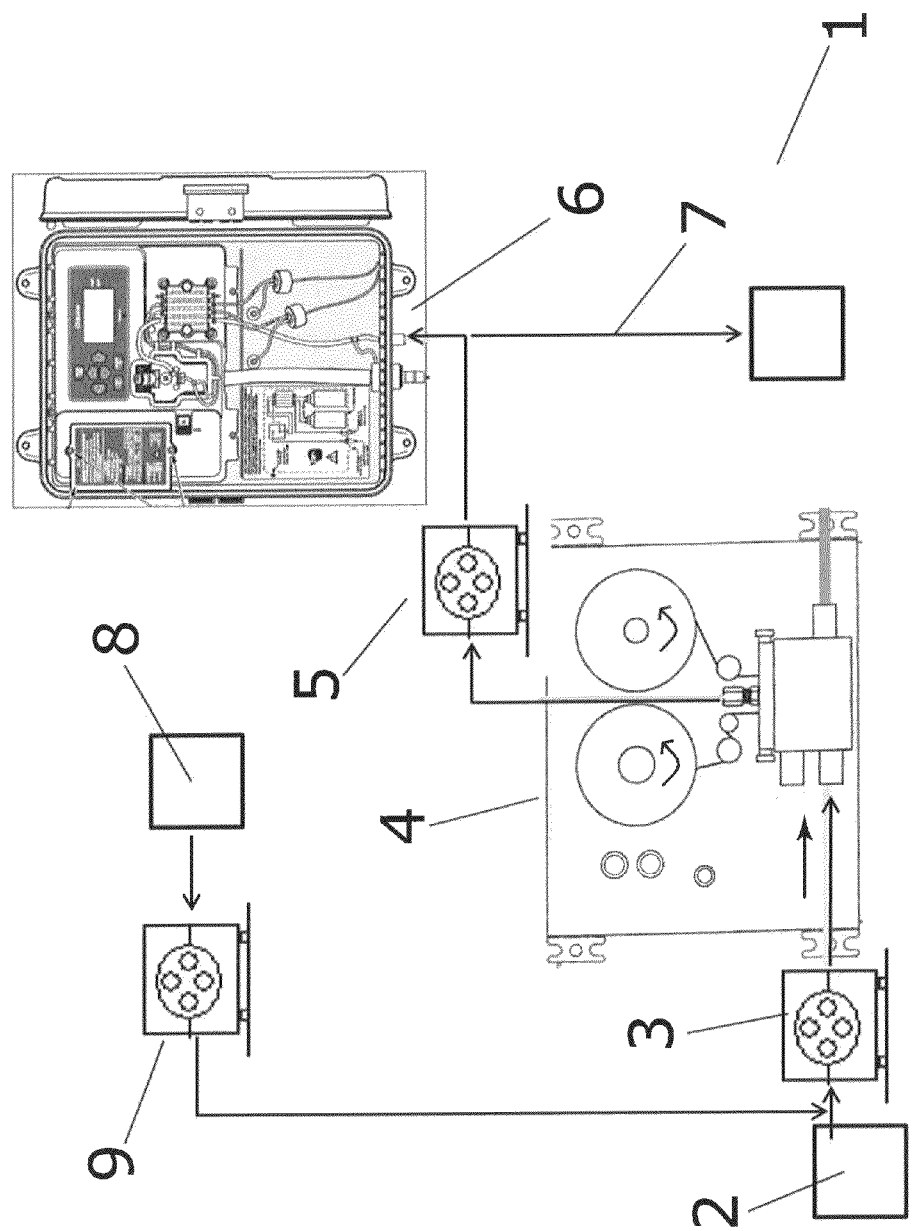
FIG. 1 is a schematic drawing of a continuous feed analyzer system using a chemical cleaning mechanism.

The following definitions are provided to determine how terms used in this application, and in particular how the claims, are to be construed. The organization of the definitions is for convenience only and is not intended to limit any of the definitions to any particular category.

"Bandstrip Filter" means a filter mechanism constructed and arranged to include a bandstrip that contains sized apertures to effect a specific degree of filtration, the bandstrip can be rolled over a fluid flow path such that only a portion of the bandstrip is in contact with the fluid and is doing the actual filtering and that portion can be readily changed by rolling the bandstrip thereby avoiding fouling of the filter due to the short exposure time of the bandstrip portion to the fluid being filtered.

"Biocide" means an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2). As used herein, the term "high level biocide" refers to a compound or composition that kills substantially all organisms, except high levels of bacterial spores, and is effected with a chemical germicide cleared for marketing as a sterilant by the Food and Drug Administration. As used herein, the term "intermediate-level biocide" refers to a compound or composition that kills mycobacteria, most viruses, microorganisms and bacteria, with a chemical germicide registered as a tuberculocide by the Environmental Protection Agency (EP). As used herein, the term "low-level biocide" refers to a compound or composition that kills some viruses and bacteria microorganisms with a chemical germicide registered as a hospital disinfectant by the EPA.

"Distal" is the opposite of "Proximal" and means subsequent to a particular step in a sequential process.

"Fouling" means the undesirable presence of or deposition of any organic or inorganic material in the water or on a surface.

"Microorganism" is a broad term whose meaning includes any organism small enough to insinuate itself within, adjacent to, on top of, or attached to equipment in contact with or adjacent to process water, it includes but is not limited to those organisms so small that they cannot be seen without the aid of a microscope, collections or colonies of such small organisms that can be seen by the naked eye but which comprise a number of individual organisms that are too small to be seen by the naked eye, as well as one or more organisms that can be seen by the naked eye, it includes but is not limited to any organism whose presence, in some way impairs the industrial process such as forming biofilms, scale, crusts, and the like.

"Monitor" means a device constructed and arranged to measure at least one physical or chemical characteristic and to output a signal or display in response to that measurement.

"Port" means a fluidic flow path which may be sealable and may be in the form of a hole, opening, valve, pipe, sluice, duct, and/or other aperture constructed and arranged for fluid to flow through.

"Proximal" is the opposite of "Distal" and means prior to a particular step in a sequential process.

In the event that the above definitions or a description stated elsewhere in this application is inconsistent with a meaning (explicit or implicit) which is commonly used, in a dictionary, or stated in a source incorporated by reference into this application, the application and the claim terms in particular are understood to be construed according to the definition or description in this application, and not according to the common definition, dictionary definition, or the definition that was incorporated by reference. In light of the above, in the event that a term can only be understood if it is construed by a dictionary, if the term is defined by the *Kirk-Othmer Encyclopedia of Chemical Technology,* 5th Edition, (2005), (Published by Wiley, John & Sons, Inc) this definition shall control how the term is to be defined in the claims.

Figure 2:
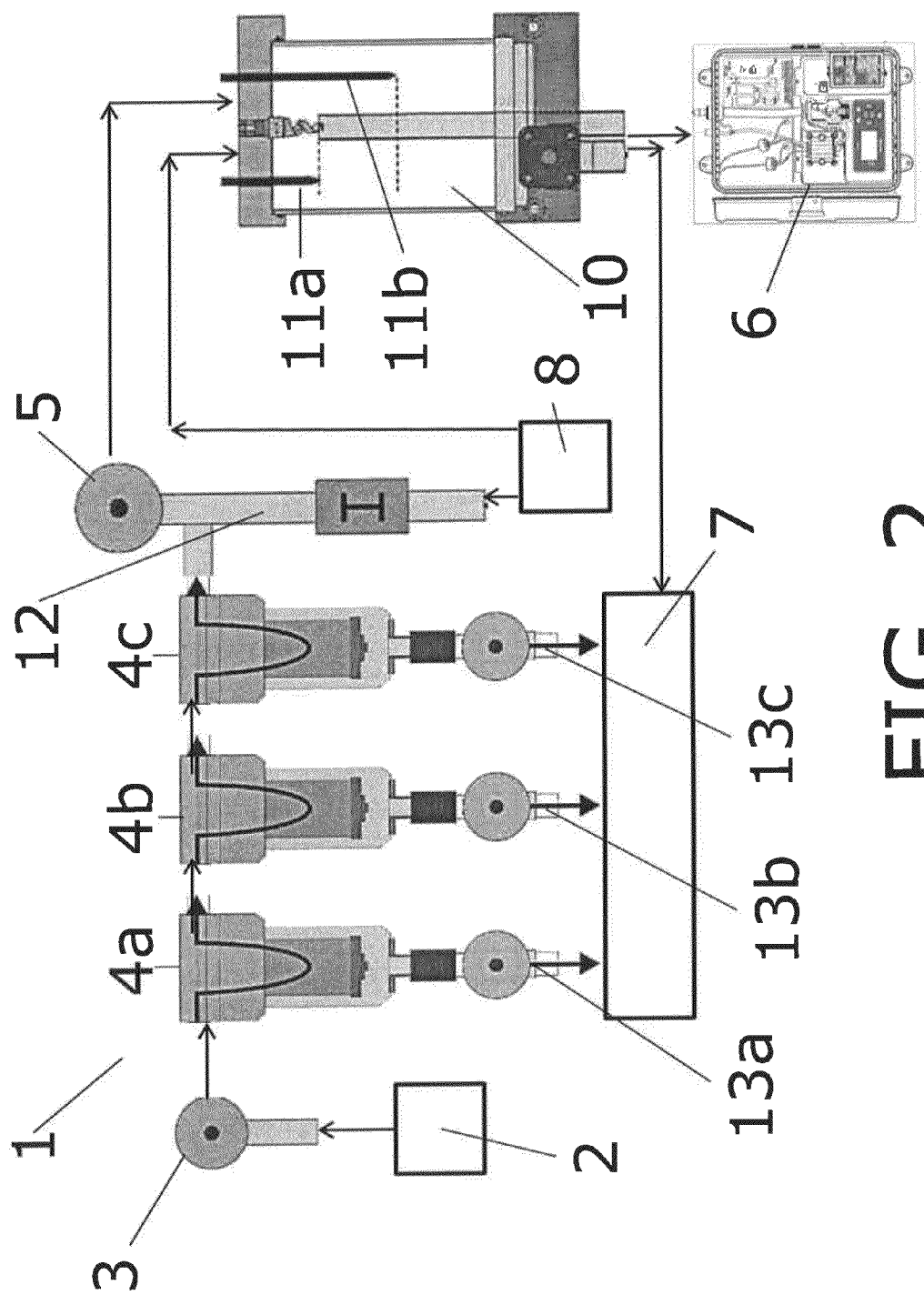
FIG. 2 is a schematic drawing of a continuous feed analyzer system using an intermediate buffer tank system to tank to allow continuous measurements.

Referring now to FIGS. 1 and 2 there are shown at least one embodiment of a method and apparatus (1) for accurately determining the amount of oxidant in a volume of fluid. The fluid flows from a source (2) and undergoes one or more pre-filtering processes prior to analysis by a prior art oxidant analyzer or a "doctrine of equivalents" equivalent. The pre-filtering is accomplished by passing the fluid through a filter array (4). The filter may flow under due to the effects of one or more pumps (3). The pre-filtering removes materials that would otherwise foul the analyzer (6) or which would render the measurement inaccurate. Each of the filters may be of different sizes, including but not limited to 300-10 micron in size such as 200 micron, 125 micron, and 50 micron. In at least one embodiment a fourth or more filters are added. The purpose of the different size of filters is to make a gradual filtration of the sample otherwise the system would plug very quickly and hence would not be workable. At the same time the pre-filtering is done in a manner that does not alter the oxidant content of a sample so the oxidant sample is truly representative of the water volume being analyzed.

In at least one embodiment the fluid source is a volume of process water from a paper mill. Such process water is typically highly turbid and contains large amounts of cellulose and other fibers, paper and wood solids, fillers, minerals, and various property enhancing additives, all of which overwhelm and make impossible accurate and/or long term analysis of the oxidant content of the process water. This in turn makes the addition of oxidants "blind" and is therefore either too much and needlessly wasteful (and possibly toxic) or too little and not sufficiently effective.

As shown in FIG. 1, in at least one embodiment the pre-filtration is accomplished by the use of one or more band filters. Bandfilters are known in the art as a filter apparatus that allows the liquid to always pass through a clean filtering material. This cleanliness is achieved because the band itself is a long strip that is constantly pulled (much like the tape in a cassette tape) across an aperture through which the liquid flows. Because it is pulled, the same given filtering surface is only in contact with the liquid for a short period of time and does not have time for significant fouling to occur. Commonly used bandfilters are at least in part held in place against the aperture by a pressure gradient pulling the band in the same direction as the liquid flow. In at least one embodiment this gradient is caused by a pump (5) downstream from the filter (4). Often the band is in a loop that includes a cleaning stage the same section of band will cycle past the aperture again and again, but because it is constantly cleaned, the effect is a perpetually clean filter surface through which the liquid flows.

In at least one embodiment a bandfilter passes the aperture at a rate of between 0.51 cm per minute to 11 cm per hour. In at least one embodiment the bandfilter is constructed and arranged to be used with liquids In at least one embodiment, the liquids that pass through the filter do not exceed 2% (meaning 2% fibers and most/all of the remaining 98% is water). In at least one embodiment the filter is rotated and is continuously washed so turbidity inducing materials do not clog up the filter.

In at least one embodiment there is only one filter. In at least one embodiment two or more filters are positioned in series with each other relative to the flow path of the water. The multiple serially positioned filters remove ever-increasing proportions of the turbidity inducing materials from the water sample.

In at least one embodiment the filters are so effective at reducing the effects of turbidity inducing materials that process waters having a solids content as high at 6% can effectively be measured. In at least one embodiment the one or more filters are arranged to remove the turbidity inducing materials from a sample that is from 2-4% solids.

In at least one embodiment the analyzer (6) downstream from the filters is a HACH CL17 colorimetric analyzer (using reagents) or one having the same characteristics, capabilities, and/or technical specifications. Alternatively, a 'reagent less' analyzer can also be used.

In at least one embodiment the flow rate of the water samples through the one or more filters are constructed and arranged to match the optimal flow rate for the analyzer. For example in the HACH CL17, the analyzer measures residuals at 3-minute intervals and the flow rate is adjusted to accommodate that rate. In at least one embodiment if the flow rate of the water samples exceeds the measuring rate of the analyzer, a portion of the water sample is diverted down a spillway (7)

and the remainder is the optimal amount which is passed on to the analyzer. In this way a flow rate that is greater than the interval rate of the analyzer can provide accurate readings. In at least one embodiment the spillway is constructed and arranged to always assure that liquid passes into the analyzer at a fixed rate.

In at least one embodiment a cleaning cycle is available to the system. The cleaning cycle allows one or more of the sensor, hoses, pumps, filters, etc. . . . to be maintained in a clean state. As various parts of the system continuously receive potentially infested water, microbial slimes may accumulate along various surfaces that contact with this infested water. In at least one embodiment the cleaning cycle can be achieved by diverting the process flow water away from one or more portions of the system and instead introducing a liquid stream that is highly concentrated with oxidant or other biocide.

In at least one embodiment concentrated sodium hypochlorite (or another oxidant or biocide) is introduced to at least one portion of the system and it cleans that portion. In at least one embodiment, concentrated sodium hypochlorite (or another oxidant or biocide) is introduced to at least one portion of the system, and the introduced sodium hypochlorite (or another oxidant or biocide) continues on to subsequent downstream portions of the system and cleans those downstream portions. This allows one insertion of a chemical to accomplish effective cleaning of multiple portions of the system. In at least one embodiment the concentrated sodium hypochlorite (or another oxidant or biocide) is introduced into a process stream which is upstream of at least one of the pre-filtering steps. In at least one embodiment a spray fluid (which can be sodium hypochlorite, or another oxidant or biocide or water) (8) is introduced by its own pump (9).

In at least one embodiment the sample water pump (3), post filter pump (5), and the cleaning cycle pump (9) are coordinated to run at the same time with different flow rates, in at least one embodiment the sample water pump (3) runs at a flow rate of between 75 to 250 times as great as the post filter pump (5). In at least one embodiment the cleaning cycle pump (9) runs at a flow rate of between $3*10^{-7}$ to $6*10^{-7}$ times more slowly than the sample water pump (3). In an exemplary embodiment the sample water pump (3) runs at a rate of 1 liter per minute, the post filter pump (5) runs at 5-10 ml per minute, and the cleaning cycle pump (9) runs at a rate of 30 ml per 12 hours.

Even after this slime-removing stream is no longer flowing through the sensor, much higher oxidant concentrations may persist for a while. In at least one embodiment the sensor (or process control equipment that is in communication with the sensor) is designed to reject as inaccurate oxidant readings until after either a time interval which is a multiple of the time interval of the sensor or until the detected oxidant levels are back down to close to what they were (for example within 0%-50% of what they were) before the cleaning cycle was initiated. In at least one embodiment the time interval is between 1 and 7 minutes long.

At least one possible example of the cleaning process is as follows: The cleaning cycle pump (9) pumps hypochlorite (and/or another oxidant or biocide) to clean some or all of the hoses and the analyzer (6). As a result the analyzer detects chlorine levels are higher than typical (for example >5 ppm). After a communication with the process control system for the apparatus (1), the apparatus switches into a static state for an interval of time (for example 30 minutes). After the time interval has lapsed, the process control system returns the apparatus back to a regular state.

Referring now to FIG. 2 there is shown a method and apparatus (1) for accurately determining the amount of oxidant in a volume of fluid. In this apparatus a sample tank (10) is present and the apparatus' constituent components are configured to allow for continuous analysis even when undergoing a cleaning cycle.

A fluid sample (2) is fed in a distal direction into a series of two or more sequential filters (4a, 4b, 4c). The sample may optionally be introduced through the use of a sample pump (3). There may be 2, 3, or more sequential filters. The sequential filters (4a, 4b, 4c) can be constructed and arranged to have varying pore sizes to effect different degrees of filtering. For example a coarse filter (4a) can a more proximally positioned filter which provides for a most coarse degree of filtering, a fine filter (4c) can be for most fine degree of filtering, and one or more intermediate filter(s) (4b) proximal to the fine filter (4c) and distal to the coarse filter (4a) and can be for gradually filtering for particles that are various degradations between coarse and fine.

None, one, some, or all of the filters can also be bandstrip filters. In at least one embodiment the pore bearing surfaces of the filters are tensioned to provide precise aperture sizes. The tension can be achieved with spring mounts pulling on them. The filters may also comprise a drain port. The drain port allows for the removal of slurry or cake that contains material incapable of passing through the filter. The drain port may comprise a sealable valve. The valves may be seated valves, check valves, knife valves, any combination thereof, and any sort of valve known in the art. Distal to the filter may be a post filter pump (5) which can pull fluid out from the filter(s).

The apparatus may comprise distal to at least one filter a flusher (12). The flusher can be used to effect a user friendly non-disruptive cleaning cycle. The flusher facilitates the feeding of a cleaning fluid/spray fluid (8) into the filter array in a direction opposite of the flow of sample fluid (proximal direction). The cleaning fluid may be water, a biocide, an oxidant, gas, and/or any other composition useful in cleaning process systems. The cleaning fluid may be introduced via a pump. A valve may be present to alternatively determine whether it is the flusher fluid (8) or the sample tank (10) which is in fluidic communication with one or more filters (4a, 4b, 4c), in at least one embodiment the flusher (12) is constructed and arranged to feed gas into the filter which can help break cake off of a filter surface.

In at least one embodiment the sample source (2) is fed at a pressure of between 0.5 to 8 Bar, preferably 1 to 3 Bar. In at least one embodiment the flow of sample into the apparatus is continuous.

In at least one embodiment the spray fluid (8) added to the apparatus is air or gaseous. The alternation between liquid pressing against the filters and gas pressing against the filters energizes the cleaning effect and better removes cake from the filters. In at least one embodiment each filter has its own discrete drain (13a, 13b, 13c), so if a valve between sequential filters is closed, it allows for one filter to be cleaned without contaminating the next filter with the dislodged cake. In at least one embodiment the cleaning effect may be enhanced by one or more filters which can help further pull cake and spray fluid out of the filter.

In at least one embodiment at least one filter (4, 4a, 4b, 4c) is a cross-filter. In at least one embodiment the filters are cleaned according to a timed sequence. The timed sequence can be initiated by a timer, by control logic, and/or a logic event.

In at least one embodiment, proximal to the filters, the filtered sample passes into a sample tank (10). Sample fluids may have an entry rate optimal for efficient filtering and may have an exit rate to the monitor (6) at a rate optimal for the monitor. The entry rate can be greater, lessor, or equal to the exit rate and either can change as appropriate or over time. The sample tank may have an entry port to receive spray fluid (8) for cleaning and a drain (7).

Within the sample tank (10) are at least two probes, one being a high level probe (11a) and one being a low level probe (11b). The system can keep track of the fluid levels within the sample tank (10) to assure continuous flow by adding fluid to the tank if the sample level drops below the low level probe (11a). It can also drain away fluid if the sample level goes above the high level probe (11b). In at least one embodiment the probes are electrical sensors, optical sensors, pressure sensors, it) piezoelectric sensors, and any combination thereof.

In at least one embodiment the oxidant measured by the monitor is a species of chlorine. The invention addresses a common problem inherent with monitoring oxidants. Many monitors utilize amperometric measurements using a sensor comprising copper, platinum and/or gold electrodes. When in contact with a reducing amount of an oxidant such as HOCl or OCl⁻ an electrical current is generated. This current is in direct linear proportion to the amount of residual chlorine present in the sample. However, when solids are present in the sample fluids, the electrodes or other portions of the monitors become fouled and result in erroneous measurements. In at least one embodiment, the apparatus removes sufficient solids from the sample to substantially improve the accuracy of an oxidant monitor's readings. In at least one embodiment, the apparatus removes sufficient solids from the sample to effectively prevent any solids based errors ors from occurring in the oxidant monitor's readings.

While this invention may be embodied in many different forms, there described in detail herein specific preferred embodiments of the invention. The present disclosure is an exemplification of the principles of the invention and is not intended to limit the invention to the particular embodiments illustrated. All patents, patent applications, scientific papers, and any other referenced materials mentioned herein are incorporated by reference in their entirety. Furthermore, the invention encompasses any possible combination of some or all of the various embodiments described herein and incorporated herein.

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10; that is, all subranges beginning with a minimum value of 1 or more, (e.g. 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

This completes the description of the preferred and alternate embodiments of the invention. Those skilled in the art may recognize other equivalents to the specific embodiment described herein which equivalents are intended to be encompassed by the claims attached hereto.

What is claimed is:

1. A method of accurately detecting the presence and concentration of chlorine in a turbid water sample, the method comprising the steps of:
    passing the water sample through at least one filter device at an entry rate,
    then passing the water sample into a sample buffer tank, and then on to a chlorine monitor, the sample tank constructed and arranged to pass water on to the monitor at an exit rate,
    detecting the presence and concentration of chlorine in the water sample with the chlorine monitor;
    wherein at least some of the time, the exit rate is different than the entry rate,
    wherein a fluid sprayer is in communication with the filter device, the fluid sprayer is constructed and arranged to pass a spray fluid into the at least one filter device in a direction opposite to that which the water sample exits the filter device, the fluid is water, biocide, gas, or any combination thereof; and
    wherein the at least one filter device is distal to a distal member, the filter device has in fluidic communication a sealable entry port in fluidic communication with the distal member, an exit port, and a sealable draining port, the draining port is proximal to the exit port and is distal to the entry port, wherein when spray fluid enters the filter device through the exit port the entry port is sealed and the draining port is opened and thereby if the spray fluid removes cake from the second filter device the cake does not come into contact with the distal member, wherein when the entry point is open sample water can pass from the distal member to the filter device, the distal member is another filter device, a pump, a conduit, or a sample water source.

2. The method of claim 1 in which there are a series of two or more filter devices the filter devices constructed and arranged to remove turbidity inducing material but not chlorine from the water sample, the filter devices in fluidic communication with each other and are sequentially ordered to progressively apply an ever more fine degree of filtration as the sample moves distally.

3. The method of claim 2 in which the sample tank comprises a high level point and a low level point and has at least one sensor array which can determine if the water surface in the sample tank is above the high level point in which case a drain port in the tank is opened to drain out water, and if the water surface in the sample tank is below the low level point in which case the drain port in the tank is closed to raise the water surface, the sensor array comprises at least one sensor that can determine if the water surface is located by at least one of the level points.

4. The method of claim 1 in which at the time that the entry port is sealed, sample water is still continuously flowing at a constant rate to the monitor.

5. The method of claim 4 in which the times at which the spray fluid is passed into the at least one filter device is coordinated to assure that the spray fluid flow will cease and that the sample water will again pass through the at least one filter device before the water surface drops below the low level point.

6. The method of claim 1 in which the entry flow rate is sufficient for effective filtration but is incompatible with the flow rate requirements for proper operation of the monitor.

7. The method of claim 1 in which the flow exit flow rate is sufficient for proper operation of the monitor but is incompatible with the flow rate required for effective filtration of the sample water.

8. The method of claim 1 in which the water sample is water from a paper mill process stream, clarified process water, influent, effluent, wastewater, or any combination thereof.

9. The method of claim 1 in which the turbidity inducing material is selected from the list consisting of: cellulose fibers, mineral fillers, property enhancing polymers, sizing agents, wood chips, silica, glass fibers and any combination thereof.

10. The method of claim 1 in which the filtered water sample is also monitored to measure one item selected from the list consisting of: concentration of a non-chlorine oxidant, pH, oxidation reduction potential, peroxide content, sulfite content, and any combination thereof.

11. The method of claim 1 in which the filtration of the water sample prevents the monitor from providing an erroneous measurement of chlorine in the sample.

12. The method of claim 1 in which the filter device comprises a surface having a plurality of pores sized to allows the passage of chlorine bearing water but to catch at least some turbidity causing matter on the surface as cake.

13. The method of claim 1 in which the filter device comprises a surface having a plurality of pores sized and positioned to allows the passage through it of chlorine bearing water but to catch at least some turbidity causing matter on the surface as cake and the surface is located in fluidic communication with and distal to the entry port and proximal to the exit port.

\* \* \* \* \*